United States Patent [19]
Mueller et al.

[11] Patent Number: 5,746,786
[45] Date of Patent: May 5, 1998

[54] POLY-1-N-ALKENYLAMINES, AND FUEL AND LUBRICANT COMPOSITIONS CONTAINING THEM

[75] Inventors: Hans-Joachim Mueller, Gruenstadt; Bernd Lothar Marczinke, Speyer; Roger Klimesch, Alsbach-Haehnlein; Michael Roeper, Wachenheim; Lothar Franz, Mutterstadt; Peter Schreyer, Weinheim; Juergen Thomas, Fussgoenheim; Juergen Mohr, Gruenstadt; Knut Oppenlaender, Ludwigshafen; Wolfgang Guenther, Mettenheim, all of Germany

[73] Assignee: BASF Aktiengesellschaft, Ludwigshafen, Germany

[21] Appl. No.: 532,810

[22] PCT Filed: Apr. 11, 1994

[86] PCT No.: PCT/EP94/01113

§ 371 Date: Oct. 23, 1995

§ 102(e) Date: Oct. 23, 1995

[87] PCT Pub. No.: WO94/24231

PCT Pub. Date: Oct. 27, 1994

[30] Foreign Application Priority Data

Apr. 22, 1993 [DE] Germany ............... 43 13 088.7

[51] Int. Cl.$^6$ ........................................ C10L 1/22
[52] U.S. Cl. ................. 44/412; 44/426; 44/432; 44/434
[58] Field of Search ................. 44/412, 426, 432, 44/434; 525/375, 379, 381; 528/392, 396, 422, 423; 252/50; 508/545, 558

[56] References Cited

U.S. PATENT DOCUMENTS

| 3,275,554 | 9/1966 | Wagemaar | 508/558 |
| 4,832,702 | 5/1989 | Kummer et al. | 44/412 |

FOREIGN PATENT DOCUMENTS

| 0 062 940 | 3/1982 | European Pat. Off. |
| 0 541 176 | 11/1992 | European Pat. Off. |
| 2125039 | 5/1971 | Germany |
| 2245918 | 9/1972 | Germany |

*Primary Examiner*—Jacqueline V. Howard
*Assistant Examiner*—Cephia D. Toomer
*Attorney, Agent, or Firm*—Oblon, Spivak, McClelland, Maier & Neustadt, P.C.

[57] ABSTRACT

Fuel and lubricant compositions contain a poly-1-n-alkenylamine as an additive.

19 Claims, No Drawings

POLY-1-N-ALKENYLAMINES, AND FUEL AND LUBRICANT COMPOSITIONS CONTAINING THEM

This application is a 371 of PCT/EP 941/01113, filed Apr. 11, 1994.

The present invention relates to poly-1-n-alkenylamines and fuel and lubricant compositions which contain poly-1-n-alkenylamines.

Polybutenylamines and their use as fuel and lubricant additives have been known for a very long time and are described, for example, in U.S. Pat. No. 3 275 554 and DE-A-2 125 039.

The prior art polybutenylamines are prepared by halogenation of polybutenes and reaction of the halides with amines. In the preparation of these products, ionic halides are formed and have to be very substantially removed.

There has therefore been no lack of attempts in the prior art to improve the known products, especially since not only does the elimination of the ionic halide require expensive measures but also considerable amounts of halogen always remain in the reaction products (cf. DE-A-2 245 918).

EP 244 616 B1 discloses polyisobutenylamines which are very useful as fuel and lubricant additives. The polyisobutenes required for the preparation of these additives are, however, difficult to obtain owing to the fact that the starting material isobutene is available only by means of expensive processes.

It is an object of the present invention to provide fuel or lubricant compositions which prevent deposits in the intake system of gasoline engines, have a particularly good dispersant effect and furthermore are technically readily obtainable.

We have found that this object is achieved by a fuel or lubricant composition which contains at least one poly-1-n-alkenylamine of the formula I

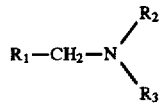
(I)

where $R_1$ is a poly-1-n-alkene radical derived from one or more 1-n-alkenes of 3–6 carbon atoms and 0–50% by weight of ethene and $R_2$ and $R_3$ may be identical or different and are each hydrogen, aliphatic or aromatic hydrocarbons, primary or secondary, aromatic or aliphatic aminoalkylene radicals or polyaminoalkylene radicals, polyoxyalkylene radicals, heteroaryl or heterocycyl radicals or, together with the nitrogen atom to which they are bonded, form a ring in which further hetero atoms may be present.

A preferred embodiment of the invention provides a fuel or lubricant composition containing at least one poly-1-n-alkenylamine of the formula I, where $R_1$ has the is abovementioned meanings and $R_2$ and $R_3$ are identical or different and are each hydrogen, alkyl, aryl, hydroxy-alkyl, an aminoalkylene radical of the formula II

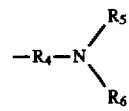
(II)

where $R_4$ is an alkylene radical and $R_5$ and $R_6$ are identical or different and are each hydrogen, alkyl, aryl or hydroxyalkyl, or a polyaminoalkylene radical of the formula III

(III)

where radicals $R_4$ are identical or different and the radicals $R_5$ are identical or different and $R_4$, $R_5$ and $R_6$ have the abovementioned meanings and m is an integer of from 1 to 7, or a polyalkylene radical of the formula IV

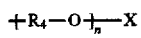
(IV)

where the radicals $R_4$ may be identical or different and have the abovementioned meanings, X is $C_1$–$C_6$-alkyl or H and n is an integer from 1 to 30, or where $R_2$ and $R_3$, together with the nitrogen atom to which they are bonded, form a morpholinyl, pyridyl, piperidyl, pyrrolyl, pyrimidinyl, pyrrolinyl, pyrrolidinyl, pyrazinyl or pyridazinyl radical.

A particularly preferred embodiment provides a fuel or lubricant composition containing at least one poly-1-n-alkenylamine of the formula I

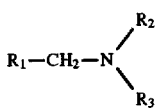
(I)

where $R_1$ is a poly-1-alkene radical of 20 to 400 carbon atoms which is derived from one or more 1-n-alkenes of 3–6 carbon atoms and 0–50% by weight of ethene and $R_2$ and $R_3$ are identical or different and are each hydrogen, $C_1$–$C_{10}$-alkyl, phenyl, naphthyl, $C_1$–$C_{10}$-hydroxyalkyl, an aminoalkylene radical of the formula II

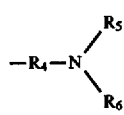
(II)

where $R_4$ is a $C_2$–$C_{10}$-alkylene radical and $R_5$ and $R_6$ are identical or different and are each hydrogen, $C_1$–$C_{10}$-alkyl, phenyl, naphthyl or $C_1$–$C_{10}$-hydroxy-alkyl, a polyaminoalkylene radical of the formula III

(III)

where the radicals $R_4$ are identical or different, the radicals $R_5$ are identical or different, $R_4$, $R_5$ and $R_6$ have the above meanings and m is an integer from 1 to 7, or a polyoxyalkylene radical of the formula IV

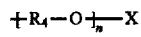
(IV)

where the radicals $R_4$ are identical or different and have the above meanings, X is $C_1$–$C_6$-alkyl or H and n is an integer of from 1 to 30, or where $R_2$ and $R_3$ together with the nitrogen atom to which they are bonded, form a morpholinyl radical.

A further particularly preferred embodiment provides a fuel or lubricant composition containing at least one poly-1-n-alkenylamine of the formula I, where $R_1$ is a poly-1-n-alkene radical, in particular of 32 to 200 carbon atoms, derived from one or more 1-n-alkenes of 3 or 4 carbon atoms and 0–40% by weight of ethene, and $R_2$ and $R_3$ are identical or different and are each hydrogen, methyl, ethyl, n-propyl, isopropyl, n-butyl, sec-butyl, isobutyl, tert-butyl, pentyl, hexyl, phenyl,

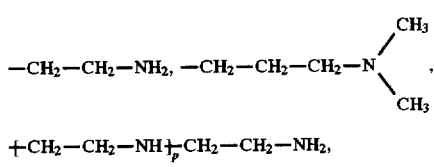

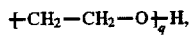

where p is an integer of from 1 to 7, in particular from 1 to 3.

where q is an integer of from 1 to 30, or, together with the nitrogen atom to which they are bonded, form a morpholinyl radical.

Particularly advantageous fuel or lubricant compositions are those containing at least one poly-1-n-alkenylamine of the formula I which is obtainable by polymerization of 1-n-alkenes in the presence of a metallocene catalyst of the formula V $$Cp_mMX_nY_r \quad V$$

where Cp is an unsubstituted or substituted cyclopentadiene ring, M is a transition metal of group 4 b, X is hydrogen or $C_1-C_6$-alkyl, Y is halogen, m is 1–3, n is 0–3, r is 0–3 and m+n+r corresponds to the valency of M, subsequent hydroformylation of the poly-1-n-alkene formed and amination of the hydroformylated reaction product under hydrogenating conditions.

Particularly preferred fuel or lubricant compositions are those which contain a poly-1-n-alkenylamine I in which $R_1$ is derived from a polypropylene or an ethene-1-butene copolymer.

Where the present invention relates to a fuel composition, in particular a fuel for internal combustion engines, the poly-1-n-alkenylamine of the formula I may be present, for example, in an amount of 10–5,000, in particular 100–800, mg/kg of fuel.

The poly-1-n-alkenylamine may be present in the novel lubricant composition, for example, in an amount of 0.5–5, in particular 1–3, % by weight, based on the total weight of the composition.

The present invention also relates to poly-1-n-alkenylamines of the formula I

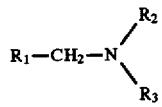

where $R_1$ is a poly-1-n-alkene radical derived from one or more 1-n-alkenes of 3–6 carbon atoms and 0–50% by weight of ethene, in particular from propene or an ethene/1-butene mixture, and $R_2$ and $R_3$ are identical or different and are each hydrogen, $C_1-C_{10}$-alkyl, phenyl, naphthyl, $C_1-C_{10}$-hydroxyalkyl, an aminoalkylene radical of the formula II

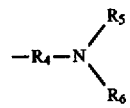

where $R_4$ is a $C_1-C_{10}$-alkylene radical and $R_5$ and R6 are identical or different and are each hydrogen, $C_1-C_{10}$-alkyl, phenyl, naphthyl or $C_1-C_{10}$-hydroxyalkyl, a polyaminoalkylene radical of the formula III

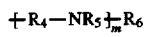

where the radicals $R_4$ are identical or different, the radicals $R_5$ are identical or different, $R_4$, $R_5$ and $R_6$ have the above meanings and m is an integer of from 1 to 7, or a polyoxyalkylene radical of the formula IV

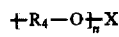

where the radicals $R_4$ are identical or different and have the above meanings, X is $C_1-C_6$-alkyl or H and n is an integer of from 1 to 30, or where $R_2$ and $R_3$, together with the nitrogen atom to which they are bonded, form a ring in which further hetero atoms may be present.

The present invention finally also relates to the use of the poly-1-n-alkenylamines of the formula I, where $R_1$, $R_2$ and $R_3$ have the abovementioned meanings, as additives in fuel or lubricant compositions, in particular for internal combustion engines.

The compounds of the formula I can be prepared, for example, by first polymerizing a 1-n-alkene in the presence of a metallocene catalyst of the formula V

where Cp is an unsubstituted cyclopentadienyl unit and/or a mono-$C_1-C_4$-alkylcyclopentadienyl unit, M is a zirconium or hafnium atom and the ligands X are hydride and/or halide ions and/or methyl, and in the presence of an aluminoxane cocatalyst, employing the catalyst and the aluminoxane cocatalyst in a ratio which corresponds to an M/Al atomic ratio of from 1:250 to 1:1000 and using temperatures of from 50° to 110° C. and a pressure of from 30 to 100 bar.

The catalysts V are zirconocenes and hafnocenes and therefore complexes of tetravalent zirconium and hafnium in which the metal atom M is bonded in the form of a sandwich between two unsubstituted and/or $C_1-C_4$-monoalkyl-substituted cyclopentadienyl groups Cp, the remaining valences of the central atom M being saturated by hydride and/or halide ions and/or by methyl groups. Zirconocene and hafnocene catalysts which are particularly preferably used in the novel process are those whose cyclopentadienyl groups are unsubstituted. The halide ions bonded to the metal atom may be fluoride, chloride, bromide and/or iodide anions.

Examples of suitable catalysts are: $Cp_2ZrF_2$, $Cp_2ZrCl_2$, $Cp_2ZrCl_2$, $Cp_2ZrI_2$, $Cp_2ZrCl$, $Cp_2Zr(CH_3)Cl$, $Cp_2Zr(CH_3)_2$, $Cp_2HfF_2$, $Cp_2HfCl_2$, $Cp_2HfBr_2$, $Cp_2HfJ_2$, $Cp_2HfHCl$, $Cp_2Hf(CH_3)Cl$ and $Cp_2Hf(CH_3)_2$.

Advantageously, only one catalyst is used in the oligomerization, but it is also possible to use mixtures of different catalysts. Preferred ligands X are chloride, hydride and methyl, and zirconium is particularly preferred as the central atom M for the catalyst V. Zirconocene chloride of the formula $Cp_2ZrCl_2$ whose cyclopentadienyl groups are unsubstituted is particularly preferably used as the catalyst.

The catalysts can be synthesized in a simple manner by known processes, for example according to Brauer (Editor): Handbuch der Praiparativen, Anorganischen Chemie, Volume 2, 3rd Edition, pages 1395 to 1397, Enke, Stuttgart 1978.

The cocatalysts used are organoaluminum compounds, preferably aluminoxanes. Aluminoxanes are formed in the partial hydrolysis of organoaluminum compounds, for example those of the formulae $AlR_3$, $AlR_2Y$ and $Al_2R_3Y_3$, in which R may be, for example, $C_1$–$C_{10}$-alkyl, preferably $C_1$–$C_5$-alkyl, $C_3$–$C_{10}$-cycloalkyl, $C_7$–$C_{12}$-aralkyl or alkylaryl and/or phenyl or naphthyl and Y may be hydrogen, halogen, preferably chlorine or bromine, or $C_1$–$C_{10}$-alkoxy, preferably methoxy or ethoxy. The partial hydrolysis of such organoaluminum compounds can be carried out by various processes, for example by the process of DE-A 3 240 383 or by that stated in EP-A 268 214. The resulting oxygen-containing aluminoxanes are in general not pure compounds but oligomer mixtures of the formula VI

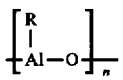
VI where, as a rule, n is from 6 to 20 and R has the above-mentioned meanings. If organoaluminum compounds having different radicals R or mixtures of organoaluminum compounds having different radicals R are hydrolysed, aluminoxanes having different radicals R are formed and may likewise be used as cocatalysts. However, aluminoxanes are advantageously used as cocatalysts. A preferably used aluminoxane is methylaluminoxane. Since, owing to their method of preparation, the aluminoxanes used as cocatalysts are not pure compounds, the molarity of aluminoxane solutions is related to their aluminum content below.

For the polymerization, the catalyst and the cocatalyst are used in an amount which corresponds to an M/Al atomic ratio of in general from 1:250 to 1:1000, preferably from 1:300 to 1:600, in particular from 1:400 to 1:500.

The polymerization of the 1-n-alkene is advantageously carried out in the liquid phase and in a solvent, advantageously with the use of small amounts of a solvent, preferably of an aliphatic or aromatic hydrocarbon, such as bezene, toluene, xylene, ethylbenzene, cumene, naphthalene, tetralin, hexane, heptane, octane, isooctane, nonane, decane, dodecane, cyclohexane, decalin, petroleum ether or ligroin. Particularly preferably used solvents are toluene and xylene. In this process, solvent/1-n-alkene volume ratios of in general from 1:20 to 1:500, preferably from 1:30 to 1:200, particularly preferably from 1:40 to 1:100 are established, the volume of the 1-n-alkene relating to its volume at the particular pressure applied. The 1-n-alkene is liquid under the conditions used.

The polymerization is generally carried out at from 50° to 110° C., particularly preferably at from 60° to 90° C., and at from 30 to 100 bar, preferably at from 30 to 50 bar. The metallocene/1-n-alkene ratio is generally not crucial for the process, but is expediently from 1:50 to 1:250000, preferably from 1:70 to 1:200000, in particular from 1:90 to 1:190000.

The polymerization process can be carried out both batchwise, for example in stirred autoclaves, or continuously, for example in tubular reactors. After the catalyst has been separated off by distillation of the products or by hydrolysis thereof followed by filtration of the precipitated solids, the reaction mixture is advantageously worked by up distillation, if desired under reduced pressure.

The propene preferably used as a raw material in this process may originate from a variety of sources, for example from crack gases, eg. from steam crack gas. Propene as formed, for example, in propane dehydrogenation may also be used. Propene may be used in purified form but also as mixtures with other hydrocarbons which are inert under the conditions of the reaction.

The polymerization process permits the selective preparation of poly-1-n-alkenes having terminal double bonds, in particular the selective preparation of propene polymers with high productivity.

The poly-1-n-alkenes, in particular the copolymers of ethene and 1-n-alkenes, can also be prepared by other known processes, as described, for example, in EP 0441 548 A1. Here too, a metallocene catalyst is used in combination with an aluminoxane. Cyclopentadienyl transition metal compounds of the formula V are likewise used here as metallocenes, preferred transition metals being Ti, Zr and Hf.

The poly-1-n-alkenes prepared are distilled if necessary and then hydroformylated in a conventional manner, using a rhodium or cobalt catalyst in the presence of CO and $H_2$ at from 80° to 200° C. and CO/$H_2$ pressures of up to 600 bar.

The reaction product (oxo product) is then aminated under hydrogenating conditions. The amination reaction is advantageously carried out at 80°–200° C. and up to 600, preferably 80–300, bar.

In the hydroformylation and amination reaction, a suitable, inert solvent is advantageously used in order to reduce the viscosity of the reaction mixture. Suitable solvents are in particular low-sulfur aliphatic, cycloaliphatic and aromatic hydrocarbons. Aliphatic solvents which are free of sulfur compounds and contain less than 1% of aromatics are particularly preferred. They have the advantage that no heat of hydrogenation is evolved at high amination temperatures and no hydrogen is consumed. In the amination and hydroformylation reaction, the solvent content is from 0 to 70% by weight, depending on the viscosity of the polymer and of the solvent. Higher dilutions are just as uneconomical as replacement of the solvent between hydroformylation and amination.

The oxo product formed in the hydroformylation reaction is usually present as an aldehyde/alcohol mixture. It may be further processed as a mixture or may be completely hydrogenated beforehand to improve its shelf life. Completely hydrogenated products are less reactive.

Owing to their preparation, the poly-1-n-alkenylamines used in the novel fuels or lubricants contain no halogen and furthermore have no unsaturated components, making them particularly suitable for use in fuels or lubricants.

Owing to their structure, the novel poly-1-n-alkenylamines have both a dispersant and a detergent effect. This means that, as detergents, they have a keep-clean effect in valves and carburetors or injection systems. When these dispersants enter the lubricant circulation of the engine via the combustion chamber, they help to improve the dispersing of sludge in engine oil.

If it is intended primarily to utilize the dispersant properties of the poly-1-n-alkenylamines, they may also be combined with conventional detergents as further additives.

In principle, any known products suitable for this purpose may be used as the detergent component in the mixture containing the novel substances as dispersants, such products being described, for example, in J. Falbe and U. Hasserodt, Katalysatoren, Tenside und Mineralöladditive, G. Thieme Verlag Stuttgart 1978, page 221 et seq. or in K. Owen, Gasoline and Diesel Fuel Additives, John Wiley & Sons 1989, page 23 et seq.

N-Containing detergents, for example compounds which contain an amino or amido group, are preferably used. Polyisobutylamines according to EP 0 244 616, ethylenediaminetetraacetamides and/or -imides according to EP 0 188 786 or polyetheramines according to EP 0 244 725 are particularly suitable, reference being made to the definitions in these publications. As a result of their preparation, the products described there likewise have the advantage of being chlorine-free and chloride-free.

If it is intended primarily to utilize the detergent effect of the novel compounds, these substances may also be combined with carrier oils. Such carrier oils are known, particularly suitable ones being polyglycol-based carrier oils, for example corresponding ethers and/or esters, as described in U.S. Pat. No. 5 004 478 or DE 38 38 918 A1. Polyoxyalkylenemonools having terminal hydrocarbon groups (U.S. Pat. No. 4 877 416) or carrier oils as disclosed in DE 41 42 241 A1 may also be used.

Suitable fuels for gasoline engines are leaded and in particular unleaded regular and premium grade gasoline. The gasolines may also contain components other than hydrocarbons, for example alcohols, such as methanol, ethanol or tert-butanol, and ethers, eg. methyl tert-butyl ether. In addition to the novel poly-1-n-alkenylamines to be used according to the invention, the fuels also contain, as a rule, further additives, such as corrosion inhibitors, stabilizers, antioxidants and/or further detergents.

Corrosion inhibitors are generally ammonium salts of organic carboxylic acids, which tend to form films owing to the fact that the starting compounds have the appropriate structure. Amines for reducing the pH are also frequently present in corrosion inhibitors. Heterocyclic aromatics are generally used for protecting non-ferrous metals from corrosion.

Testing of the novel poly-1-n-alkenylamines with regard to their suitability as valve cleaners is carried out by means of engine tests using a 1.2 l Opel Kadett engine.

EXAMPLES

1. Preparation of poly-1-n-alkenes 1.1 30 ml of a 1.5 molar solution of methylaluminoxane in toluene were initially taken in a 2 l stirred autoclave, 900 ml (13.3 mol) of liquid propene were condensed therewith and the mixture was heated to 60° C. The resulting pressure was 20 bar. Thereafter, 40.5 mg (0.17 mmol) of zirconocene (dicyclopentadienylzirconium dichloride), dissolved in 7 ml of a 1.5 molar solution of methylaluminoxane in toluene, were added and oligomerization was effected in the course of 60 minutes. The aluminum/zirconium atomic ratio was 250:1. A yield of 590 ml of propene oligomers was obtained. The productivity of the catalyst under the reaction conditions used, expressed as ml of product per g of catalyst per hour, was 11,900. Gas chromatographic analysis of the product gave the following composition:

| Oligomers | $C_6$: | 16.3% |
|---|---|---|
| | $C_9$: | 24.1% |
| | $C_{12}$: | 16.5% |
| | $C_{15}$: | 5.9% |
| | $C_{18}$: | 2.3% |
| | $\geq C_{21}$: | 34.9% |

Analysis of the resulting products by infrared and NMR spectroscopy shows that only hydrocarbons having terminal double bonds which are predominantly localized in vinylidene groups were formed.

Examples 2 to 4 were carried out similarly to Example 1, the various aluminum/zirconium atomic ratios stated in the Table being used.

| Example | Zirconocene [mmol] | Methylaluminoxane [mmol] | Al/Zr atomic ratio | Productivity [ml of product per g caat. per h] |
|---|---|---|---|---|
| 1.2 | 0.17 | 90 | 530 | 14600 |
| 1.3 | 0.07 | 30 | 430 | 18600 |
| 1.4 | 0.07 | 60.5 | 860 | 20100 |

EXAMPLE 1.5

30 ml of a 1.5 molar solution of methylaluminoxane in toluene were initially taken in a 1 l stirred autoclave, 500 ml (6.3 mol) of liquid 1-n-butene were condensed therewith and the mixture was heated to 80° C. The resulting pressure was 13 bar. 0.1 mol of ethylene was then metered in. After the addition of 28 mg (0.096 mmol) of zirconocene, oligomerization was effected for 30 minutes.

551 ml of a butene-ethylene oligomer were isolated.

2. Hydroformylation 2.1 The propene oligomer prepared according to Example 1.1 was distilled and the fraction $\geq C_{21}$ was hydroformylated without a solvent at two different temperatures (120° and 160° C.) at 280 bar. Starting material Iodine number: 49 g of iodine/100 g A) High-pressure hydroformylation at 120° C.

A solution of 4.5 g of 85% strength cobalt carbonyl in 700 g of polypropene [0.18% of cobalt] was reacted in a 2.5 l autoclave having a lift-type stirrer for 5 hours at 120° C. and a CO/H$_2$ pressure of 280 bar. In order to separate off the cobalt catalyst, the reaction mixture was let down and then stirred for one hour with the same volume of a 10% strength acetic acid solution at from 90° to 95° C. with passage of air, and the cobalt-containing aqueous phase was separated off.

The oxo product had the following characteristics:

Iodine number: 8.6 g of iodine/100 g

CO number: 67 mg KOH/g

OH number: 1 mg KOH/g

Conversion: 80%

Yield: 85.5% (determined by column chromatography)

B) High-pressure hydroformylation at 160° C. Procedure as for A Characteristics of oxo product:

Iodine number: 0.1

CO number: 2.5 under acidic conditions at elevated temperatures

CO number: 2.5 under alkaline conditions at room temperature

OH number: 40

Conversion: 99.8% 2.2 The butene-ethylene oligomer prepared according to Example 1.5 was hydroformylated batchwise using cobalt under the following conditions:

The starting material [iodine number 53] was used in the form of a 30% strength solution in toluene.

Apparatus: 2.5 l autoclave with lift-type stirrer

Temperature: 160° C.

Pressure: 260–280 bar CO/H$_2$ 1:1

Cobalt: 0.18% in the feed

Cobalt as: carbonyl

Time: 5 hours

To separate off the cobalt catalyst, the reaction mixture was let down and then stirred for one hour with the same volume of 10% strength acetic acid solution at from 90° to 95° C. with passage of air, and the cobalt-containing phase was then separated off. The solvent was then removed under reduced pressure.

| % a) Yield | % Conversion | Iodine number | CO number | OH number | Acid number |
|---|---|---|---|---|---|
| 96 | 98.7 | 0.7 | 15 | 55 | 1.2 | a) Determined by column chromatography

3. Amination 3.1 760 ml of $NH_3$ (liquid) and 75 g of Raney nickel were added to 400 g of the hydroformylation product according to Example 2.1A in a stirred autoclave, and heating was carried out for 4 hours at 180° C. and at a $H_2$ pressure of 280 bar. After filtration, the product had the following characteristics:

Amine number: 60.5

Secondary and tertiary amine number: 1.6

OH number: 7.7

3.2 300 g of the hydroformylation product according to Example 2.1A were heated with 40 g of diethylenetriamine, 150 g of cyclohexane and 50 g of Raney nickel in a stirred autoclave at 180° C. for 4 hours and at a $H_2$ pressure of 280 bar. After filtration and evaporation of the solvent, the residue had the following characteristics:

Amine number: 115.0

Secondary and tertiary amine number: 44.6

OH number: 6.1

4. Engine tests

The engine tests were carried out in an Opel Kadett 1.2 1 engine. The fuel used was European premium grade unleaded fuel.

| Additive | Dose | Deposits in intake valves, in mg | | | |
|---|---|---|---|---|---|
| | | Valves 1 | 2 | 3 | 4 |
| Polypropyleneamine according to Example 3.1 | 800 ppm | 0 | 0 | 0 | 0 |
| Base value without additive | | 830 | 384 | 338 | 750 |

This shows that the novel polyalkenylamines have an excellent effect as a detergent.

5. Spot test

A 3% strength by weight mixture of the polypropyleneamine according to Example 3.1 with a dispersion of carbon black in a mineral oil was prepared by heating to 50° C. for 1 hour. The dispersion thus obtained was developed on a filter paper in the same way as a chromatogram. The area of pure oil and that of distributed carbon black were compared (description of test: Les Huiles pour Moteurs et le Fraissage des Moteurs, A. Schilling, Vol. 1, page 89 et seq., 1962).

| Additive content of carbon black dispersion [% by weight] | Proportionate areas of carbon black [%] |
|---|---|
| 0 | 22 |
| 3 | 45 |

The test clearly shows the dispersant properties of the novel poly-1-n-alkenylamines.

We claim:

1. A composition, which comprises a fuel and at least one poly-1-n-alkenylamine of the formula I

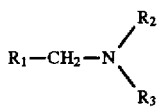

where $R_1$ is a poly-1-n-alkene radical derived from one or more 1-n-alkenes of 3–6 carbon atoms and 0–50% by weight of ethene and $R_2$ and $R_3$ may be identical or different and are each hydrogen, hydroxyalkyl, aliphatic or aromatic hydrocarbons, primary or secondary, aromatic or aliphatic aminoalkylene radicals or polyaminoalkylene radicals, polyoxyalkylene radicals, heteroaryl or heterocyclyl radicals, or together with the nitrogen atom to which they are bonded, form a ring in which further hetero atoms may be present, wherein the poly-I-alkenylamine is obtained by a process comprising a) polymerization of 1 -n-alkene in the presence of a metallocene catalyst of the formula V $$Cp_mMX_nY_r \quad V$$

where Cp is an unsubstituted or substituted cyclopentadiene ring, M is a transition metal of group 4 b, X is hydrogen or $C_1$–$C_6$-alkyl, Y is halogen, m is 1–3, n is 0–3, r is 0–3 and m+n+r correspond to the valency of M;

b) subsequent hydroformylation of the poly-1-n-alkene; and c) amination of the reaction product from reaction step b) under hydrogenating conditions.

2. The composition of claim 1, wherein $R_2$ and $R_3$ are identical or different and are each hydrogen, alkyl, aryl, hydroxyalkyl, an aminoalkylene radical of the formula II

where $R_4$ is an alkylene radical and $R_5$ and $R_6$ are identical or different and are each hydrogen, alkyl, aryl, hydroxyalkyl, a polyaminoalkylene radical of the formula III $$+R_4-NR_5\!\!\!\!+_{\overline{m}}R_6 \qquad (III)$$

where the radicals $R_4$ are identical or different, the radicals R, are identical or different, $R_4$, $R_5$ and $R_6$ have the abovementioned meanings and m is an integer of from 1 to 7, or a polyalkylene radical of the formula IV $$+R_4-O+_{\overline{n}}X \qquad (IV)$$

where the radicals $R_4$ may be identical or different and have the above-mentioned meanings, X is $C_1$–$C_6$-alkyl or H and n is an integer from 1 to 30, or where $R_2$ and $R_3$, together with the nitrogen atom to which they are bonded, form a morpholinyl, pyridyl, piperidyl, pyrrolyl, pyrimidinyl, pyrrolinyl, pyrrolidinyl, pyrazinyl or pyridazinyl radical.

3. The composition of claim 1, wherein $R_1$ is a poly-1-n-alkene radical of 20 to 400 carbon atoms which is derived from one or more 1-n-alkenes of 3–6 carbon atoms and 0–50% by weight of ethene and $R_2$ and $R_3$ are identical or different and are each hydrogen, $C1-C_{10}$-alkyl, phenyl, naphthyl, $C_1-C_{10}$-hydroxyalkyl, an aminoalkylene radical of the formula II

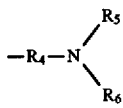  (II)

where
$R_4$ is a $C_2-C_{10}$-alkylene radical and
$R_5$ and R6 are identical or different and are each hydrogen, Cl-C,O-alkyl, phenyl, naphthyl, $C_1-C_{10}$-hydroxyalkyl, a polyaminoalkylene radical of the formula III

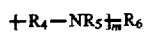  (III)

where the radicals $R_4$ are identical or different, the radicals $R_5$ are identical or different, $R_4$, $R_5$ and $R_6$ have the above-mentioned meanings and m is an integer of from 1 to 7, or a polyalkylene radical of the formula IV

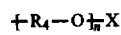  (IV)

where the radicals $R_4$ may be identical or different and have the above-mentioned meanings, X is $C_1-C_6$-alkyl or H and n is an integer from 1 to 30, or where $R_2$ and $R_3$, together with the nitrogen atom to which they are bonded, form a morpholinyl radical.

4. The composition of claim 3, where $R_1$ is a poly-1-n-alkene radical derived from one or more 1-n-alkenes of 3 or 4 carbon atoms and from 0 to 40% by weight of ethene, and $R_2$ and $R_3$ are identical or different and are each hydrogen, methyl, ethyl, n-propyl, isopropyl, n-butyl, sec-butyl, isobutyl, tert-butyl, pentyl, hexyl, phenyl,

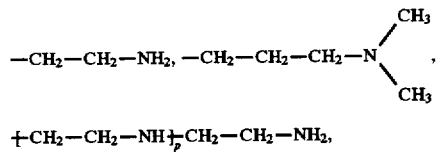

where p is an integer from 1 to 7, $+CH_2-CH_2-O+_qH$, where q is an integer from 1 to 30, or, together with the nitrogen atom to which they are bonded, form a morpholinyl radical.

5. The composition of claim 4, wherein p is an integer of from 1 to 3.

6. The composition of claim 1, which comprises at least one poly-1-n-alkenylamine wherein R, is a poly-1-n-alkene radical derived from propene or from an ethene/1-n-butene mixture.

7. The composition of claim 1, wherein said poly-1-n-alkenylamine is present in an amount of from 10 to 5,000 ppm, based on the total weight of said composition.

8. The composition of claim 7, wherein said poly-1-n-alkenylamine is present in an amount of from 100 to 800 ppm, based on the total weight of said composition.

9. The composition of claim 1, wherein said fuel comprises gasoline.

10. The composition of claim 9, wherein said gasoline is leaded gasoline.

11. The composition of claim 9, wherein said gasoline is unleaded gasoline.

12. The composition of claim 9, wherein said gasoline is premium gasoline.

13. The composition of claim 9, wherein said gasoline comprises at least one component selected from the group consisting of methanol, ethanol, tert-butanol, and methyl tert-butyl ether.

14. A composition, which comprises a fuel and at least one poly-1-n-alkenylamine of the formula I

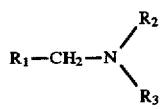  (I)

where
$R_1$ is a poly-1-n-alkene radical derived from propene or from an ethene/1-n-butene mixture and
$R_2$ and $R_3$ may be identical or different and are each hydrogen, hydroxyalkyl, aliphatic or aromatic hydrocarbons, primary or secondary, aromatic or aliphatic aminoalkylene radicals or polyaminoalkylene radicals, polyoxyalkylene radicals, heteroaryl or heterocyclyl radicals, or together with the nitrogen atom to which they are bonded, form a ring in which further hetero atoms may be present.

15. The composition of claim 14, wherein said fuel comprises gasoline.

16. The composition of claim 15, wherein said gasoline is leaded gasoline.

17. The composition of claim 15, wherein said gasoline is unleaded gasoline.

18. The composition of claim 15, wherein said gasoline is premium gasoline.

19. The composition of claim 15, wherein said gasoline comprises at least one component selected from the group consisting of methanol, ethanol, tert-butanol, and methyl tert-butyl ether.

* * * * *